United States Patent [19]
Johnston et al.

[11] 3,986,385
[45] Oct. 19, 1976

[54] APPARATUS FOR DETERMINING THE FREEZING POINT OF A LIQUID

[75] Inventors: James Stewart Johnston, Bognor Regis; Trevor Howard Neve, Arundel, both of England

[73] Assignee: Rosemount Engineering Company Limited, Bognor Regis, England

[22] Filed: July 16, 1975

[21] Appl. No.: 596,466

[30] Foreign Application Priority Data
Aug. 5, 1974 United Kingdom............... 34347/74

[52] U.S. Cl................................. 73/17 R; 73/67.1
[51] Int. Cl.²........................................ G01N 25/02
[58] Field of Search........................... 73/17 R, 67.1

[56] References Cited
UNITED STATES PATENTS

| | | |
|---|---|---|
| 2,437,194 | 3/1965 | Harrington............................. 73/17 |
| 3,201,970 | 8/1965 | Beaugh................................. 73/17 |
| 3,202,602 | 8/1965 | Beaugh................................. 73/17 |
| 3,600,933 | 8/1971 | Johnston et al........................ 73/17 |

Primary Examiner—Herbert Goldstein
Attorney, Agent, or Firm—Dugger, Johnson & Westman

[57] ABSTRACT

Apparatus for determination of the freezing point of a liquid or solution has a probe extending into the liquid with means for vibrating the probe. Fixed elements which are cooled, e.g. Peltier plates, are arranged adjacent probe so that a mantle of solid forms on these elements and grows to touch the probe, thereby changing the resonant frequency. This change in resonant frequency is sensed and used to control the cooling so that the probe remains just in contact with a surface where solid is forming, i.e. in liquid at the freezing point. The probe temperature is sensed electrically, e.g. with a resistance thermometer.

7 Claims, 3 Drawing Figures

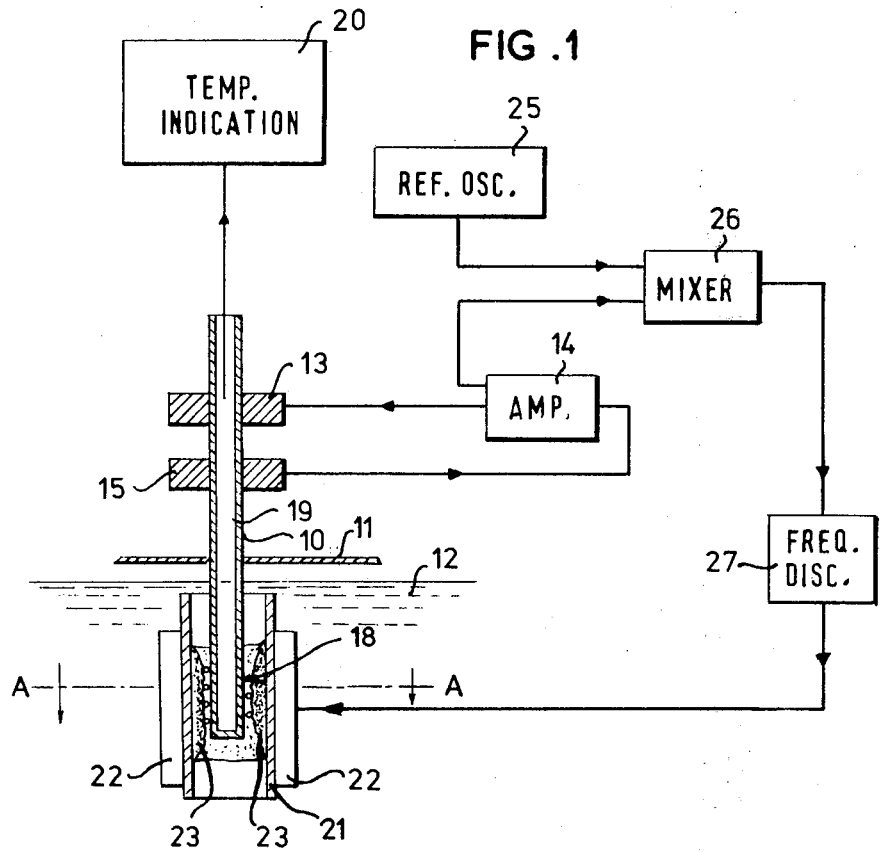
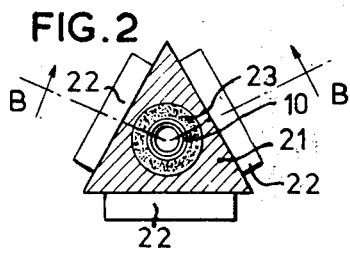
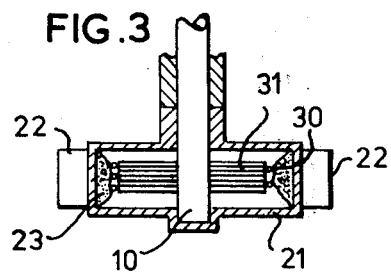

APPARATUS FOR DETERMINING THE FREEZING POINT OF A LIQUID

BACKGROUND OF THE INVENTION

1. Field of the Invention

This invention relates to apparatus for determining the freezing point of a liquid.

2. Prior Art

In our earlier Patent Specification No. 3,600,933 apparatus for the determination of the freezing point of a liquid is described comprising a probe for at least partial immersion in the liquid, means for vibrating said probe, means for cooling the probe and means responsive to the thickness of the solidified material deposited (i.e. solidified solvent in the case of a solution) on the probe and operative to control the cooling so as to maintain equilibrium conditions with a mantle of solidified material of constant thickness, and means for indicating or recording the temperature of the mantle.

When equilibrium conditions are obtained with a mantle of constant thickness, then the heat extracted by the cooling means is just sufficient to maintain the surface of the solid mantle at the freezing point. The vibration of the probe prevents supercooling. The abovedescribed apparatus has particular advantages in determining the freezing point of a solution. At the freezing point, latent heat is absorbed and there is a plateau or change in slope of the cooling curve (that is the relationship between temperature and time) as the liquid is gradually cooled. Particularly with a small sample of solution, no flat plateau is observed because, as increasing amounts of solvents freeze, the concentration of the remainder of the solution increases with a consequent decrease in the freezing point. The result is that what would have been a plateau for a pure solvent becomes a sloping line having a slope different from that of the liquid above its freezing point. The true freezing point of the solution is, in these circumstances, the temperature at which this change of the slope occurs. It is usually difficult to establish this from a graphical record and it is almost impossible to discover the change of slope in the presence of any significant degree of supercool. The above-described form of probe enables the freezing point to be determined. The probe forms a unit which can be put in the liquid in a sample cell or in a large tank and can operate automatically to provide an indication or record of the freezing point of the liquid.

In the apparatus described in the above-mentioned specification the probe itself is cooled and hence the mantle of solid material forms on the probe. It is the surface of the mantle which is at the exact temperature to be measured but this mantle will normally have a finite thickness and will extend over the temperature sensor. In order to maintain the mantle at constant thickness, heat is continuously extracted from the interior of the probe so that there is heat flow from the liquid through the mantle into the probe. In these circumstances therefore there is a slight error in the temperature sensed if the temperature sensor is beneath the surface of the mantle. This problem particularly arises with a form of probe in which, to sense the thickness of the mantle, an additional element is provided adjacent the probe so that the solid mantle, as it builds up on the probe, comes in contact with and attaches the probe to this additional element thereby changing the resonant frequency. The marked change in resonant frequency provides a very convenient means of determining when the mantle has reached a predetermined thickness. To measure the temperature at the surface of the mantle in this case, as described in the aforementioned specification, the temperature sensor may be mounted on the additional element.

SUMMARY OF THE INVENTION

The present invention relates to a modification of the apparatus described in the aforementioned specification. In the present invention, the cooling means are arranged to cool the additional element so that the mantle forms on that element and the temperature sensor is arranged on the probe. With this construction, the mantle builds up on the additional element until it is of such thickness that it comes in contact with the probe whereupon the resonant frequency changes; this change in the resonant frequency is used to control the cooling. When equilibrium conditions are reached, there is no net heat flow through the probe. Heat flow through the mantle does not affect the temperature sensor. The thickness of the mantle is immaterial and the weight of the mantle does not affect the resonant frequency of the probe. This arrangement therefore enables the freezing point to be determined even more accurately than with the arrangements described in the aforementioned specification.

Thus, according to the present invention, apparatus for the determination of the freezing point of a liquid comprises a probe for at least partial immersion in the liquid, means for vibrating said probe, an additional element adjacent said probe, means for cooling the additional element, means responsive to the change in resonant frequency of the probe when solid material deposited on the additional element comes in contact with the probe, which means are operative to control the cooling so as to maintain equilibrium conditions with a mantle of solidified material on the additional element of constant thickness and means for indicating or recording the temperature of the probe.

The additional element conveniently comprises a metal block, preferably formed of copper or other material of high thermal conductivity, with Peltier cooling cells mounted on or in the block, said block having a bore within which the probe is located. Conveniently the bore in the block is cylindrical. The probe may have a flange or ring carrying the temperature sensor, the additional element being arranged so that the mantle grows inwardly towards this ring or flange.

The temperature sensor is conveniently a resistance thermometer although other types of sensor, e.g. a thermocouple may be employed. The probe may be vibrated in an axial or torsional mode. The vibrational frequency may be ultrasonic but, with the aforementioned arrangement in which the temperature sensor is carried on a ring or flange on the probe, it is preferable to use slow torsional vibration e.g. of an audio frequency. The probe may be formed of a piezo electric element, for example of quartz or suitable ceramic, and vibrated piezo electrically by an alternating electric current applied to electrodes on the probe. Alternatively it may be formed of magnetostrictive material which may be vibrated magnetostrictively. The probe, with these arrangements may be driven by an electronic oscillator. The probe itself is preferably used as the frequency determining component of the oscillator which may therefore consist of an amplifier amplifying signals from a pick-up transducer sensing the vibration of the probe and providing an output to drive the probe. Alternatively the probe may be mechanically coupled to a separate mechanical oscillator.

For determining the change in resonant frequency of the probe, it is convenient to have a reference oscillator which oscillates at a frequency slightly different from the frequency of the probe drive. If signals from the reference frequency and the probe drive are mixed, an output is obtained having a frequency, amplitude or polarity which can be used to control the coolant system. In some cases it may be convenient to use, as the reference oscillator, a further probe for immersion in said liquid, the two probes being made mechanically similar. By this arrangement any change in resonant frequency caused by changing properties of the liquid are cancelled.

BRIEF DESCRIPTION OF THE DRAWINGS

FIG. 1 is a diagrammatic section through one form of apparatus for the determination of the freezing point of a liquid;

FIG. 2 is a transverse section along the line A-A of FIG. 1; and

FIG. 3 is a longitudinal section through a modification of the apparatus of FIG. 1.

DESCRIPTION OF THE PREFERRED EMBODIMENTS

Referring to FIGS. 1 and 2, there is shown a rod or tube 10 formed of magnetostrictive material, such as nickel or a suitable nickel alloy, which rod or tube extends through a wall 11 into liquid 12 in a tank. The part of the rod or tube in the tank thus forms a probe. This probe is maintained in axial or torsional oscillation by a coil 13 energised from an amplifier 14. The rod or tube 10 is mounted at the mid point along its length in the wall 11 of the tank so that there is a node of the axial or torsional oscillation of the rod or tube in a plane of the wall. The drive system for maintaining oscillation of the probe uses the probe itself as the frequency determining element. For this purpose there is provided a further transducer 15 sensing vibration of the probe which feeds the amplifier 14. The amplifier 14 thus operates at the resonant frequency. A resistance thermometer 18 on the probe is connected by leads 19 to a temperature indicator or recorder 20.

Surrounding the probe is a copper block 21 on which are mounted Peltier cooling cells 22. In FIG. 1, the block 21 is shown in section along the line B—B of FIG. 2, the cells 22 being indicated diagrammatically. Cooling of the block causes liquid in a cylindrical bore within the block to cool and a mantle of solid material forms on the cool surface as shown at 23 in FIG. 2. This mantle gradually grows. Eventually it will come in contact with the oscillating probe. This causes the frequency of oscillation to change. The change is sensed by mixing part of the output of the aforementioned amplifier with output from a reference oscillator 25 in a mixer 26, the signal being applied to a frequency discriminator 27 which controls the power applied to the Peltier cooling cells. The arrangement is such that, when the sudden frequency change occurs due to contact between the mantle formed within the block and the probe, the cooling power is cut off or reduced. Thus equilibrium conditions are maintained in which there is a mantle of solid material just forming adjacent the surface of the probe. The temperature sensor senses the temperature of the liquid in this region where the mantle is just forming.

The accuracy of temperature measurement can be checked by filling the tank with liquid having a known freezing point; in many cases distilled water may be suitable. Where solvents other than water are used and it is required to know the depression of freezing point for the particular concentration of solute, a preliminary measurement can be made to establish the freezing point of the pure solvent so that almost all instrumental errors can be eliminated. Once the system has been set up for a particular solution it would in general be unnecessary to change the setting of the reference oscillator even when one solution sample is changed for another. It is possible to have the sample changing continuously provided that the change is at a sufficiently slow rate that the equilibrium conditions with the mantle just coming into contact with the probe can be maintained.

Instead of having a magnetostrictive probe, a piezoelectric probe may be employed. A thermocouple may be employed in place of a resistance thermometer for temperature sensing. Instead of using Peltier cooling cells, other cooling means may be employed, for example a refrigerant may be circulated through the aforementioned block.

FIG. 3 illustrates a modification of the apparatus of FIGS. 1 and 2 in which a temperature sensor 30 comprises a resistance thermometer wound on a ring or flange 31 mounted on the vibrating rod 10. This makes it easier for the solid mantle to effect the vibration of the probe. In this case it may be preferable to use slow torsional vibrations of the probe and the vibrations therefore may be below ultrasonic frequency, for example at audio frequencies.

We claim:

1. Apparatus for the determination of the freezing point of a liquid comprising a probe for at least partial immersion in the liquid, means for vibrating said probe at a resonant frequency, an additional element adjacent said probe, said element comprising a metal block and Peltier cooling cells mounted on the block, said block having a bore within which the probe is located, means for cooling said element, means responsive to the change in resonant frequency of the probe when solid material deposited on said element comes in contact with the probe for operatively controlling the cooling means so as to establish equilibrium conditions with a mantle of solidified material on said element of constant thickness and means for measuring the temperature of the probe.

2. Apparatus as claimed in claim 1 wherein the bore in the block is cylindrical.

3. Apparatus as claimed in claim 1 wherein the probe has a flange carrying the temperature sensor, the additional element being arranged so that the mantle grows inwardly towards said flange.

4. Apparatus as claimed in claim 3 and wherein the means for vibrating the probe comprises means for vibrating the probe at an audio frequency in a torsional mode.

5. Apparatus as claimed in claim 1 wherein the means for vibrating the probe comprises an electronic oscillator for driving the probe.

6. Apparatus as claimed in claim 5 wherein the probe is used as the frequency determining component of said oscillator and wherein said oscillator comprises a pick-up transducer sensing the vibration of the probe, an amplifier amplifying signals from said transducer and providing an output to drive the probe.

7. Apparatus as claimed in claim 1 wherein, the means for vibrating the probe comprises probe drive means for vibrating the probe at a resonant frequency, and that the controlling means includes a reference oscillator which oscillates at a reference frequency slightly different from the frequency of the probe drive, and means for mixing signals from the reference oscillator and the probe drive means to obtain an output for controlling the cooling means.

* * * * *